US00PP10092P

United States Patent [19]

Trees

[11] Patent Number: Plant 10,092

[45] Date of Patent: Oct. 28, 1997

[54] NEW GUINEA IMPATIENS NAMED 'BFP-661 PURPLE'

[75] Inventor: Scott C. Trees, Arroyo Grande, Calif.

[73] Assignee: Ball Horticultural Company, West Chicago, Ill.

[21] Appl. No.: 670,744

[22] Filed: Jun. 21, 1996

[51] Int. Cl.[6] ..... A01H 5/00

[52] U.S. Cl. ..... Plt./87.6

[58] Field of Search ..... Plt./87.6

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

A new and distinct New Guinea Impatiens cultivar named 'BFP-661 Purple' is provided. This new cultivar was the result of a controlled breeding program wherein the 'Tahiti' cultivar (U.S. Plant Pat. No. 8,601) was pollinated by the 'Raspberry Rose' cultivar (U.S. Plant Pat. No. 9,212). The new cultivar forms large generally round vibrant purple flowers that display an iridescent appearance. The foliage is medium green in coloration. An attractive compact upright mounded growth habit is exhibited. The new cultivar can be readily distinguished from the parent 'Raspberry Rose' cultivar.

1 Drawing Sheet

SUMMARY OF THE INVENTION

The present invention comprises a new and distinctive Impatiens plant, botanically known as New Guinea Impatiens, and hereinafter is referred to by the cultivar name 'BFP-661 Purple'.

The new cultivar is the product of a planned breeding program. More specifically, the breeding program which resulted in the production of the new cultivar was carried out in a controlled environment during 1993 at Arroyo Grande, Calif., U.S.A. The female parent (i.e., the seed parent) was the 'Tahiti' cultivar (U.S. Plant Pat. No. 8,601) which exhibits light pink blooms, dark green foliage, and a compact growth habit. The male parent (i.e., the pollen parent) was the 'Raspberry Rose' cultivar (U.S. Plant Pat. No. 9,212) which exhibits large dark rose blooms with a white eye, medium green foliage, and a moderate growth habit. The parentage of the new cultivar can be summarized as follows:

'Tahiti'×'Raspberry Rose'.

The seeds resulting from the above pollination were sown and plantlets were obtained which were physically and biologically different from each other. Selective study resulted in the identification of a single plant of the new cultivar. This plant initially was designated BFP-661.

It was found that the new cultivar of the present invention:

(a) exhibits attractive large generally round purple flowers,
(b) forms medium green foliage,
(c) exhibits a good basal branching character, and
(d) exhibits a compact upright growth habit.

Asexual reproduction of the new cultivar by terminal or stem cuttings taken during 1994, at Arroyo Grande, Calif., U.S.A. has demonstrated that the characteristics of the new cultivar as herein described are firmly fixed and are retained through successive generations of such asexual propagation.

The 'BFP-661 Purple' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Raspberry Rose' cultivar (U.S. Plant Pat. No. 9,212), it is found that the new cultivar exhibits a shorter more compact growth habit, the flowers are slightly smaller and more purple in coloration, and the leaves generally are smaller. Also, the new variety can be readily distinguished from the 'BFP-664 Lavender' cultivar (U.S. Plant patent application Ser. No. 08/670,745, filed concurrently herewith) that is of the same parentage. More specifically, the new variety slightly less compact and generally displays smaller flowers than the 'BFP-664 Lavender' cultivar.

Plants of the new cultivar are marketed under the Celebration trademark by the Ball Horticultural Company.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at West Chicago, Ill., U.S.A.

DETAILED DESCRIPTION

The chart used in the identification of colors described herein is The R.H.S. Colour Chart of The Royal Horticultural Society, London, England. The plants were produced from cuttings taken from stock plants of the new cultivar and were transplanted during early November into 10 cm. (4 inch pots) and were grown in a soilless growth medium under standard greenhouse conditions at West Chicago, Ill., U.S.A. The greenhouse temperature was maintained at approximately 72° F. during the day and approximately 65° F. during the night. The plants were in flower eight to nine weeks later when the observations described hereafter were taken.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous, and branching.

Plant description:

*Form.*—Basal branching.

*Habit of growth.*—Compact, upright, and mounded. A mature plant commonly measures approximately 6.5 to 8 cm. in height and approximately 18 to 19 cm. in width. This compares to a height of approximately 11 to 14 cm. and width of approximately 16 to 22 cm. for the parent 'Raspberry Rose' cultivar.

*Foliage.*—The configuration is elliptic with an acuminate apex and an acuminate base. The mature leaves of the new cultivar measure approximately 7.2 to 8.5 cm. in length×approximately 3.0 to 3.6 cm. in maximal width compared to approximately 9.6 to 9.9 cm. in length ×approximately 3.5 to 3.7 cm. in maximal width for the 'Raspberry Rose' cultivar. The leaf margins are serrate (as illustrated). The mature foliage of new cultivar is medium green, Green Group 139A with lighter green veins and commonly with a midvien of Red Group 54C (adaxial), and Greyed-Green Group 191A with green veins and a midvein of Green Group 137D (abaxial). This compares to Green Group 139A (adaxial) and Green Group 137C (abaxial) for the 'Raspberry Rose' cultivar. The stem coloration is Green Group 137D with a base of Greyed-Purple Group 184D for the new cultivar. This compares to Yellow-Green Group 154A for the 'Raspberry Rose' cultivar.

Flower description:

*Flowering habit.*—Freely flowering.

*Natural flowering season.*—Throughout the year in a greenhouse environment.

*Flowers borne.*—Above foliage, arising from leaf axis.

*Flower color.*—The petals are somewhat bluer than Red-Purple Group 74A and are brighter and redder than Purple-Violet Group 80A, and the lower four petals have bases of Red Group 53C producing an eye (adaxial), and are Purple-Violet Group 80C (abaxial). This compares to Red-Purple Group 66A (adaxial) and Red-Purple Group 66C (abaxial) for the parent 'Raspberry Rose' cultivar.

*Quantity of flowers.*—Approximately 4 to 5 per axil compared to approximately 5 to 6 per axil for the 'Raspberry Rose' cultivar.

*Number of petals.*—Five, and overlapping.

*Petal shape.*—Heart-shaped, the upper three petals tend to have broad bases, and the lower two petals tend to have pointed bases.

*Flower size.*—Approximately 5.7 to 6.0 cm. in length and approximately 5.7 to 6.0 cm. in width. This can be compared to approximately 6.0 to 7.0 cm. in length and approximately 6.0 to 6.9 cm. in width for the 'Raspberry Rose' cultivar.

*Flower buds.*—Ellipsoidal in configuration, and generally covered with three sepals plus two rudimentary sepals fused into the under surface of the superior petal. A spur originating from the base of the inferior sepal is approximately 4 to 4.6 cm. in length on fully opened flowers which can be compared to approximately 5.5 to 5.8 cm. for the spur of the 'Raspberry Rose' cultivar. The spur coloration is Red-Purple Group 63A which can be compared to Red Group 42B for the 'Raspberry Rose' cultivar.

*Reproductive organs.*—The stamens are colorless. The anthers tend to be fused together forming one organ that surrounds the pistil. Commonly the anthers shed pollen prior to the stigma becoming receptive. The pollen coloration is yellow-Orange Group 19C and the ovary coloration is Green Group 141A. This can be compaared to a stamen coloration of Yellow-Green Group 154D, a pollen coloration of Yellow Group 10D, and an ovary coloration of Yellow-Green Group 144C for the parent'Raspberry Rose' cultivar.

I claim:

1. A new and distinct cultivar of New Guinea Impatiens plant named 'BFP-661 Purple', substantially as herein shown and described, which:

(a) exhibits attractive, large generally round purple flowers,
(b) forms medium green foliage,
(c) exhibits a good basal branching character, and
(d) exhibits a compact upright growth habit.

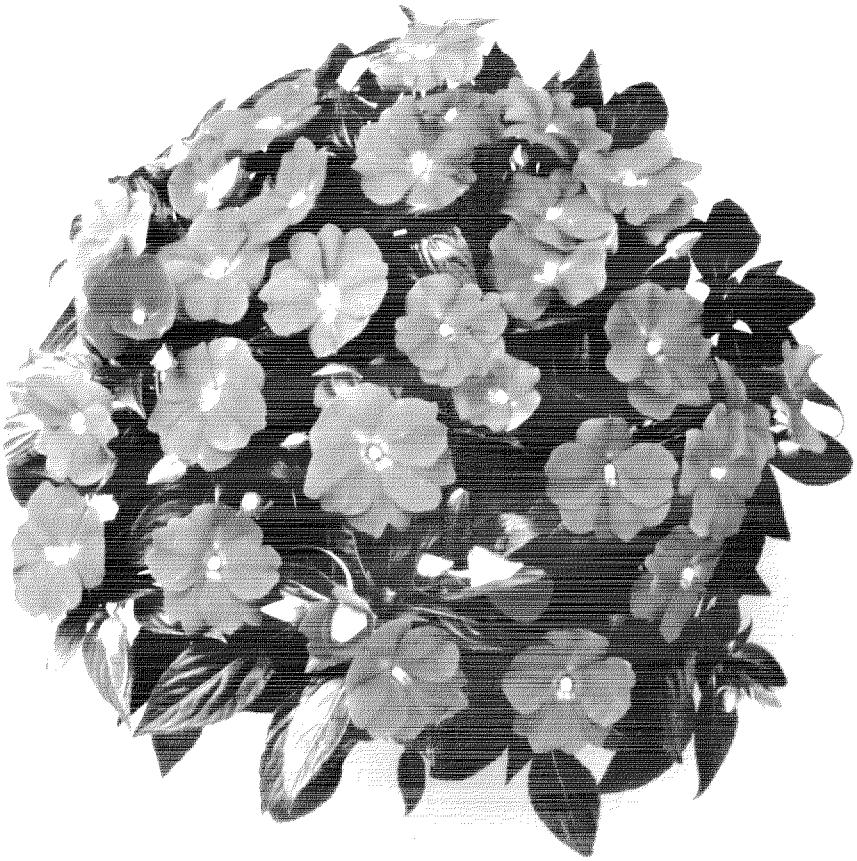

* * * * *